(12) United States Patent
Edwards et al.

(10) Patent No.: US 10,932,683 B2
(45) Date of Patent: Mar. 2, 2021

(54) NEEDLE ELECTRODE FIXATION DEVICE AND ASSOCIATED METHODS

(71) Applicant: MUSC FOUNDATION FOR RESEARCH DEVELOPMENT, Charleston, SC (US)

(72) Inventors: Jonathan Edwards, Mount Pleasant, SC (US); Jessica Barley, Mount Pleasant, SC (US); Mark Semler, Mount Pleasant, SC (US)

(73) Assignee: MUSC Foundation for Research Development, Charleston, SC (US)

(*) Notice: Subject to any disclaimer, the term of this patent is extended or adjusted under 35 U.S.C. 154(b) by 929 days.

(21) Appl. No.: 15/291,448

(22) Filed: Oct. 12, 2016

(65) Prior Publication Data

US 2017/0100047 A1  Apr. 13, 2017

Related U.S. Application Data

(60) Provisional application No. 62/240,156, filed on Oct. 12, 2015.

(51) Int. Cl.
*A61B 5/04* (2006.01)
*A61B 5/00* (2006.01)
*A61B 5/0492* (2006.01)

(52) U.S. Cl.
CPC ........ *A61B 5/04001* (2013.01); *A61B 5/0022* (2013.01); *A61B 5/0492* (2013.01); *A61B 5/688* (2013.01); *A61B 5/6849* (2013.01); *A61B 5/7203* (2013.01); *A61B 2505/05* (2013.01)

(58) Field of Classification Search
CPC ..... A61B 5/6848; A61B 5/6849; A61B 5/688; A61B 5/0492; A61B 5/04001; A61B 5/0022; A61B 5/7203; A61B 2505/05
See application file for complete search history.

(56) References Cited

U.S. PATENT DOCUMENTS

| | | |
|---|---|---|
| 6,708,050 B2 | 3/2004 | Carim |
| 6,912,424 B2 | 6/2005 | Bishay et al. |
| 6,961,603 B2 | 11/2005 | Merilainen |
| 8,170,656 B2 | 5/2012 | Tan et al. |
| 8,285,356 B2 | 10/2012 | Bly et al. |
| 8,374,669 B2 | 2/2013 | Espenhain |
| 8,386,005 B2 | 2/2013 | Schouenborg |
| 8,433,386 B2 | 4/2013 | Zhang |
| 8,628,020 B2 | 1/2014 | Beck |
| 8,798,709 B1 | 8/2014 | McCrary et al. |
| 8,805,469 B1 | 8/2014 | Bibian et al. |
| 8,805,470 B2 | 8/2014 | Afanasewicz et al. |
| 9,131,900 B2 | 9/2015 | Afanasewicz et al. |
| 2005/0277841 A1* | 12/2005 | Shennib ............... A61B 5/0444 600/511 |

(Continued)

*Primary Examiner* — Eun Hwa Kim
(74) *Attorney, Agent, or Firm* — Riverside Law LLP (57) ABSTRACT

A needle electrode fixation device is configured to secure a transdermal needle electrode to a patient. The device includes a base having a body that defines a first portion and a second portion. The first and second portions are rotatable relative to each other. The first portion defines a channel configured to fit a portion of the transdermal needle electrode. The second portion defines a recess configured to fit a tip of the needle electrode. The device further includes an adhesive layer configured to affix the base to the patient.

18 Claims, 7 Drawing Sheets

(56) References Cited

U.S. PATENT DOCUMENTS

| | | | |
|---|---|---|---|
| 2008/0275327 A1* | 11/2008 | Faarbaek | A61B 5/0002 |
| | | | 600/382 |
| 2009/0306602 A1* | 12/2009 | Elwell | A61M 25/02 |
| | | | 604/180 |
| 2010/0234713 A1 | 9/2010 | Sheraton | |
| 2011/0105876 A1* | 5/2011 | Zhang | A61B 5/0478 |
| | | | 600/373 |
| 2015/0126842 A1* | 5/2015 | Padalino | A61B 5/0492 |
| | | | 600/377 |

* cited by examiner

__NEEDLE ELECTRODE FIXATION DEVICE AND ASSOCIATED METHODS__

RELATED APPLICATION

This application claims priority to U.S. Provisional Application No. 62/240,156, filed Oct. 12, 2015, which is hereby incorporated by reference in its entirety herein.

TECHNICAL FIELD

This disclosure relates generally to a transdermal needle electrode fixation device and associated methods.

BACKGROUND

Intraoperative neuromonitoring (IONM) uses electrophysiological methods such as electroencephalography (EEG), electromyography (EMG), and evoked potentials to monitor the functional integrity of certain neural structures (e.g., nerves, spinal cord and parts of the brain). IONM reduces the risk of iatrogenic damage to the nervous system of a patient by providing functional guidance to a surgeon and/or an anesthesiologist. IONM employs transdermal needle electrodes that are inserted into the patient and connected to a control system that processes and displays the signals picket up by the electrodes.

SUMMARY

Health care providers are at risk for needle sticks from transdermal needle electrodes during patient repositioning, needle removal, and needle disposal. Because IONM may involve insertion of up to 40 needle electrodes in the patient, there are many opportunities for needle sticks. Additionally, movement of an electrode needle relative to the patient compromises recordation of neuromonitoring, potentially inhibiting a health care provider's awareness of physiological changes in the patient. The needle electrode fixation devices described herein are configured to minimize the likelihood of needle sticks and also to minimize movement of a needle electrode relative to the patient.

In a first aspect of the present disclosure, a needle electrode fixation device is configured to secure a transdermal needle electrode to a patient. The device includes a base having a body that defines a first portion and a second portion. The first and second portions are rotatable relative to each other. The first portion defines a channel configured to fit a portion of the transdermal needle electrode. The second portion defines a recess configured to fit a tip of the needle electrode. The device further includes an adhesive layer configured to affix the base to the patient.

In a second aspect of the present disclosure, a method of using a needle electrode fixation device to secure a transdermal needle electrode to a patient is disclosed. The device includes a base having a body that defines a first portion that further defines a channel in which a portion of the transdermal needle electrode is disposed and a second portion that further defines a recess in which a tip of the needle electrode is disposed. The device also includes an adhesive layer. The method includes a step of rotating the first portion of the body relative to the second portion so as remove the tip of the needle electrode from the recess. The method also includes a step of puncturing a skin surface of the patient with the tip of the needle electrode. The method also includes a step of inserting the needle electrode into a transdermal layer of the patient. The method also includes a step of affixing the needle electrode fixation device to the skin surface with the adhesive layer. The method also includes a step of removing the adhesive layer from the skin surface. The method also includes a step of withdrawing the needle electrode from the transdermal layer of the patient, the withdrawing step resulting in the tip of the needle electrode being biased into the recess so as to minimize exposure to the tip.

BRIEF DESCRIPTION OF THE DRAWINGS

The foregoing summary, as well as the following detailed description of illustrative embodiments of the needle electrode fixation device and associated methods of the present application, will be better understood when read in conjunction with the appended drawings. For the purposes of illustrating the device of the present application, there is shown in the drawings illustrative embodiments. It should be understood, however, that the application is not limited to the precise arrangements and instrumentalities shown. In the drawings.

DETAILED DESCRIPTION OF THE ILLUSTRATIVE EMBODIMENTS

Aspects of the disclosure will now be described in detail with reference to the drawings, wherein like reference numbers refer to like elements throughout, unless specified otherwise. Certain terminology is used in the following description for convenience only and is not limiting.

Figure 1A:
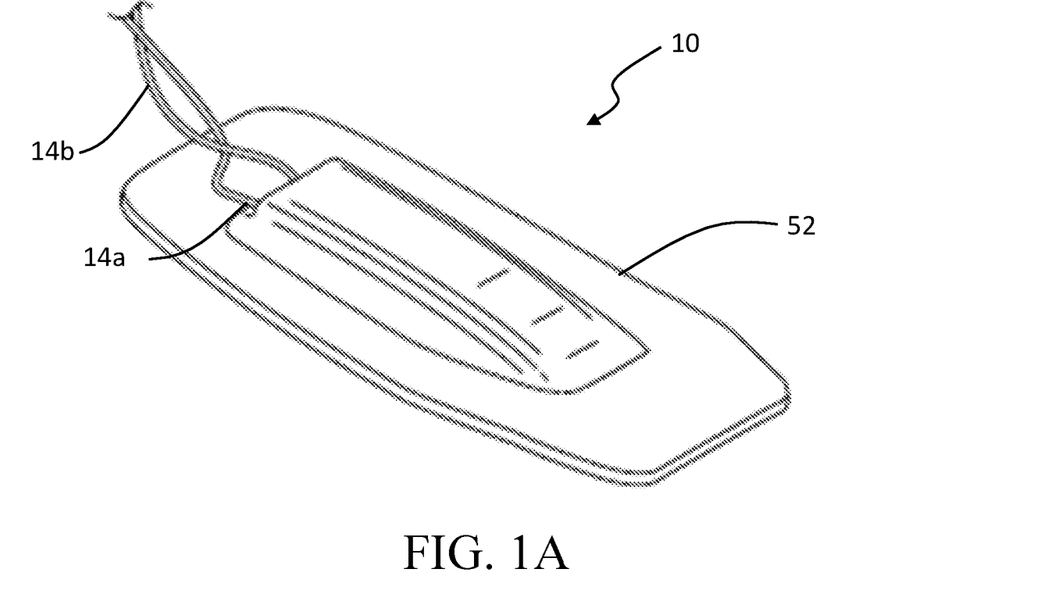
FIGS. 1A and 1B depicts a needle electrode fixation device, including a cover, an adhesive layer, a base and two needle electrodes.
Figure 1B:
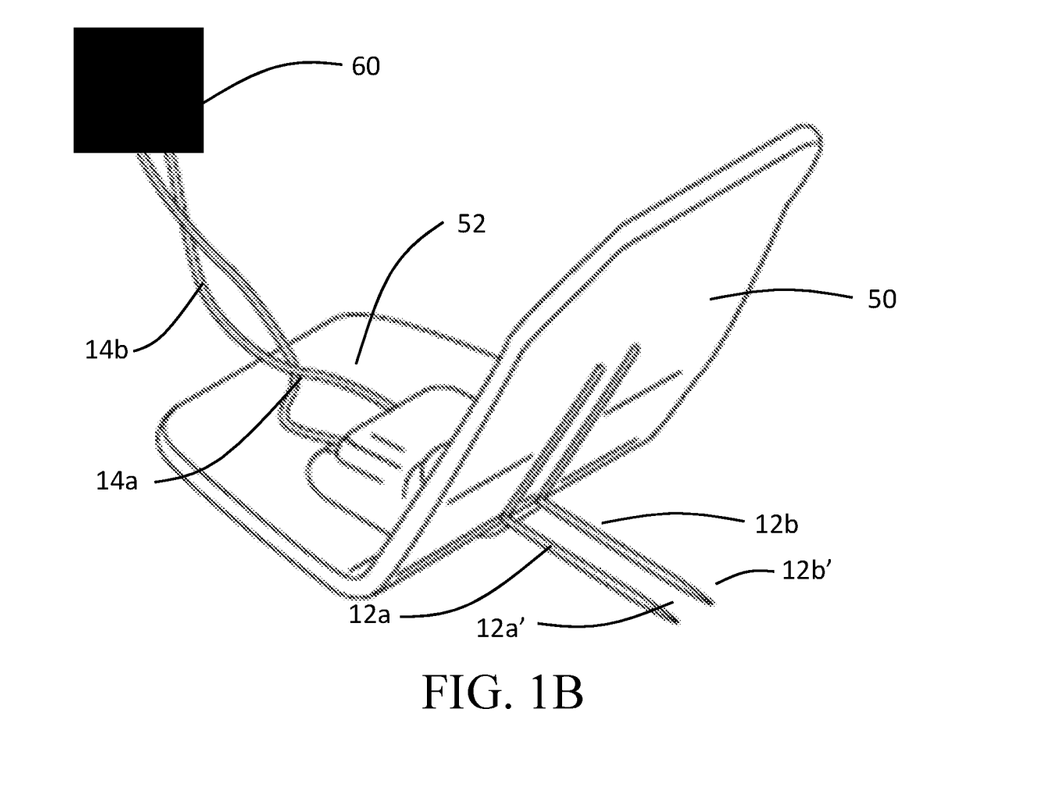

Referring to FIGS. 1A and 1B, a needle electrode fixation device 10 includes a pair of transdermal needle electrodes 12a, 12b. Needle electrodes 12a, 12b are configured for insertion into a patient for IONM. Each needle electrode 12a, 12b has a body that tapers to form a needle tip 12a', 12b' that is configured to puncture a surface of the patient's skin. The needle electrodes 12a, 12b may be attached to electrode leads 14a, 14b that connect to a control system 60 that receives signals from the needle electrodes and displays parameters based on those signals that represent physiological aspects of the patient. The embodiments described herein include two electrodes, but each of the embodiments described may be modified to include another number of electrodes, such as one, three, or four electrodes. In some embodiments, a first electrode 12a may be configured to be a ground or reference electrode and a second electrode 12b may be configured to record signals received. Alternatively, first electrode 12a may be configured to stimulate the patient and second electrode 12b may be configured to transmit the patient's response to the stimulation of first electrode 12a.

Needle electrode fixation device 10 further includes an adhesive layer 50 (shown in FIG. 1B) and a cover 52. Adhesive layer 50 is configured to secure the device 10 to the surface of the patient's skin. Adhesive layer 50 has a top adhesive surface configured to attach to a base 20 of the needle fixation device and a bottom adhesive surface configured to attach to the patient's skin. Adhesive layer 50 and its bottom layer may be comprised of biocompatible materials including acrylates (e.g., methacrylates and epoxy diacrylates) and other materials commonly used for securing bandages, wraps, and other medical devices to human skin. Cover 52 is affixed to the top of base 20 and may include an interference artifact shield configured to minimize electrical interference that might otherwise be detected by the needle electrodes 12a, 12b. Portions of the adhesive layer 50 and the cover 52 overlap the base 20 so as to together form a tab 54 that may be used to enable removal of the needle electrode fixation device 10. Flat, flexible circuitry for wireless transmission of data may also be disposed between the adhesive layer 50 and the cover 52 to provide for wireless transmission of data. For example, the flat, flexible circuitry may be disposed in the tab 54.

Figure 2A:
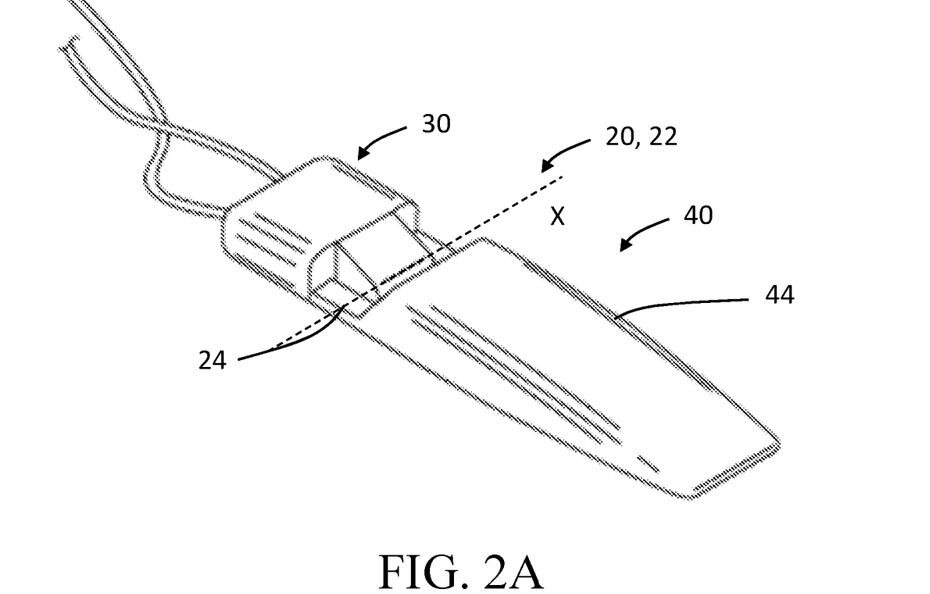
FIGS. 2A, 2B, and 2C depicts the base and two needle electrodes of the needle electrode fixation device shown in FIGS. 1A and 1B.
Figure 2B:
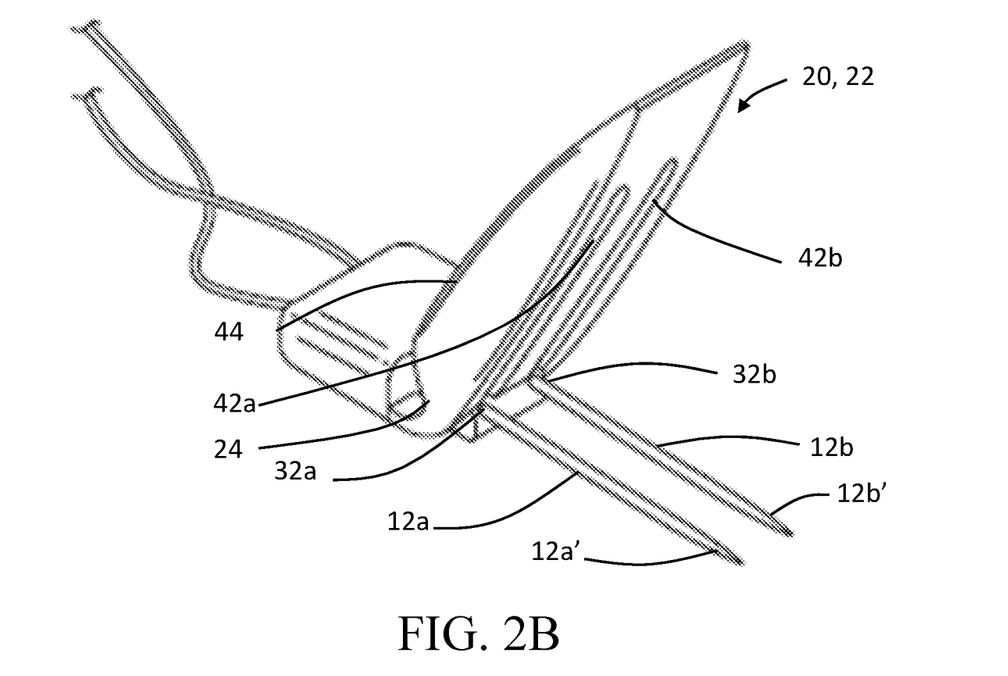
Figure 2C:
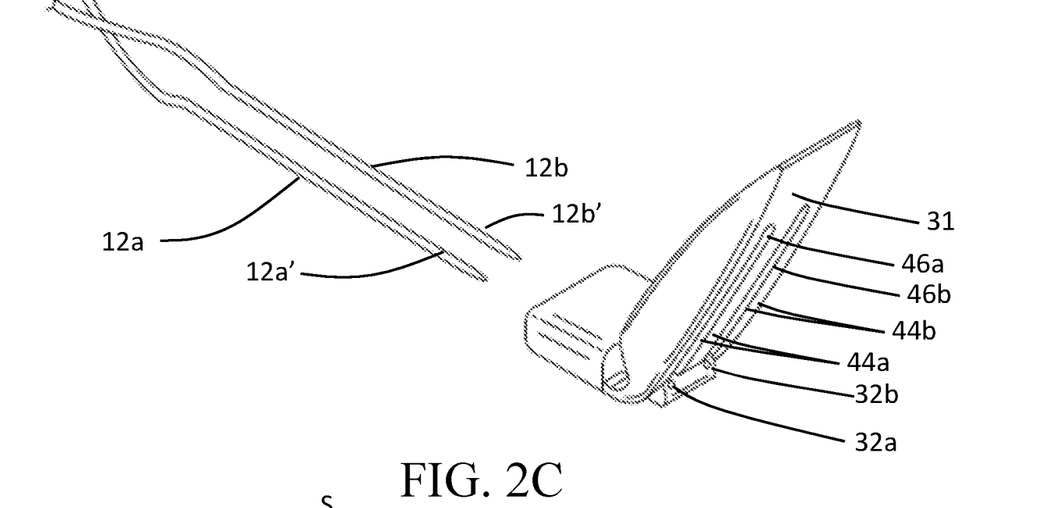

With reference to FIGS. 2A, 2B, and 2C, base 20 includes a body 22 that defines a first portion 30 and a second portion 40. The first portion 30 is configured to move relative to the second portion 40. For example, first portion 30 may be configured to rotate relative to second portion 40 about an axis X (shown in FIG. 3). First portion 30 and second portion 40 are connected to each other by a biasing member 24.

Figure 3:
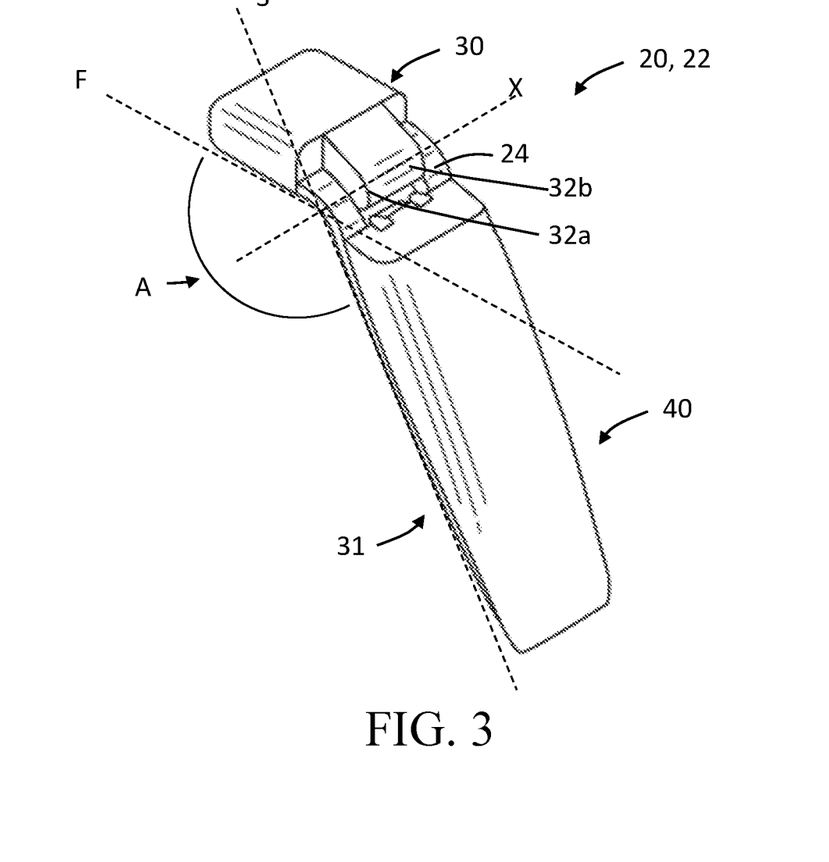
FIG. 3 depicts the base shown in FIGS. 2A, 2B, and 2C.

Referring to FIG. 3, biasing member 24 biases first portion 30 at an angle relative to second portion 40. Specifically, first portion 30 defines a bottom surface 31 that is generally planar and extends along a first line F. Second portion 40 defines a bottom surface 41 that is generally planar and extends along a second line S. First line F and second line S extend perpendicular to axis X, about which first portion 30 and second portion 40 are rotatable. Biasing member 24 is configured to bias the first portion 30 at an angle relative to second portion 40 such that, after being formed (for example, by injection molding) and prior to application of adhesive layer 50 and cover 52, first line F forms an angle A with second line S. Angle A may be between 100 and 170 degrees, such as between 120 and 160 degrees, such as between 130 and 150 degrees. After adhesive layer 50 and cover 52 are disposed on base 20, angle A is approximately 180 degrees (e.g., between 170 and 190 degrees, such as between 175 and 185 degrees) and first portion 30 and second portion 40 are biased relative to each other such that needle tips 12a', 12b' are disposed in recesses 42a, 42b (described below) unless the biasing force is overcome so as to expose needle tips 12a', 12b' for insertion into the patient.

Body 22 of base 20 is formed such that biasing member 24 biases the first portion 30 and the second portion 40 such that the device 10 is self-capping to cover needle tips 12a', 12b' when they are not inserted into the patient's skin. In some examples, device 10 may be further configured to form to curvatures of portions of the surface of the patient's skin. First portion 30 and second portion 40 may be formed with tapered sides (or no sides) such that the device 10 has a smooth upper surface in order to enhance patient comfort. Body 22, including biasing member 24, first portion 30, and second portion, may be injection molded as a single piece. For example, body 22 may be injection molded in the configuration shown in FIG. 3. In alternative embodiments, the adhesive layer 50 includes an elastic portion that biases first portion 30 and second portion 40 at angle A.

First portion 30 defines channels 32a, 32b configured to fit needle electrodes 12a, 12b, respectively. Channels 32a, 32b extend through first portion 30 parallel to first line F. Channels 32a, 32b may be circular and define diameters that are slightly larger than the diameters of needle electrodes 12a, 12b such that needle electrodes 12a, 12b pass through channels 32a, 32b and lateral movement is minimized. In alternative embodiments, first portion 30 may have a single channel that extends parallel to first line F and is large enough to fit both needle electrodes 12a, 12b.

As shown in FIGS. 2B and 2C, second portion 40 defines recesses 42a, 42b that correspond to channels 32a, 32b and are configured to fit the tips 12a', 12b' of needle electrodes 12a, 12b. Recesses 42a, 42b may each be defined by a pair of side surfaces 44a, 44b and a top surface 46a, 46b. In alternative embodiments, a single recess may be configured to fit both tips 12a', 12b'. For example, a single recess may extend between the outer of each of sidewalls 44a and 44b and be further defined by a top surface that extends between the two sidewalls. As shown in FIGS. 2A, 2B, 2C, and 3, a top portion of the body 22 separates recesses 42a, 42b such that needles 12a, 12b disposed in the recesses 42a, 42b are blocked from extending through the body 22.

Prior to use, tips 12a', 12b' of needle electrodes 12a, 12b may be inserted through channels 32a, 32b and into recesses 42a, 42b. Adhesive layer 50 may be affixed to base 20 before or after needle electrodes 12a, 12b are inserted into channels 32a, 32b. Adhesive layer 50 may have an aperture, or multiple apertures that correspond to recesses 42a, 42b such that the tips 12a', 12b' of the needle electrodes 12a, 12b can pass from recesses 42a, 42b through the adhesive layer 50. Cover 52 may also be secured to base 20 before or after needle electrodes 12a, 12b are inserted through base 20.

In one example, base 20 is first disposed on top of the top adhesive surface of adhesive layer 50. Cover 52 is then disposed on top of the base 20 and the adhesive layer 50 so as to cover any of the top adhesive surface of the adhesive layer 50 that is not covered by the base 20. Tips 12a', 12b' of needle electrodes 12a, 12b then puncture through cover 52 into channels 32a, 32b, and into recesses 42a, 42b. Before or after insertion into the base 20, needle electrodes 12a, 12b may be connected to electrode leads 14a, 14b. Alternatively, needle electrodes 12a, 12b may be inserted into base 20 prior to affixing base 20 to the top adhesive surface of the adhesive layer 50. Cover 52 may then be affixed utilizing a cutout configured such that cover 52 can wrap below the electrode leads 14a, 14b.

In order to insert electrodes 12a, 12b into the patient, base 20 is flexed about axis X so as to overcome the force of biasing member 24 and such that angle A is greater than 180 degrees and needle electrodes 12a, 12b are exposed from recesses 42a, 42b. The healthcare provider then inserts the tips 12a', 12b' of the exposed needle electrodes into the patient's skin. Once the needle electrodes 12a, 12b are inserted into the patient's skin and rotational force about axis X is released, biasing member 24 causes angle A to decrease. Specifically, second portion 40 moves relative to first portion 30 such that angle A conforms to the contours of the patient's skin. The adhesive later 50 is then affixed to the surface of the patient's skin such that second portion 40 is disposed above needle electrodes 12a, 12b.

As described above, needle electrodes 12a, 12b are connected to electrode leads 14a, 14b that send and receive signals to and from a control system 60 (shown schematically in FIG. 1B). Control system 60 may be configured to process and display electrophysiological signals as they are sensed by recording electrodes. Control system 60 may also be configured to selectively activate stimulating electrodes and process and display electrophysiological signals as they are sensed by recording electrodes. A baseline for various parameters is then established and deviations from that baseline may be used to, for example, to localize neural structures, to test function of these structures, and to detect intraoperative injury. In alternative embodiments, needle electrodes 12a, 12b may be wirelessly connected to control system 60 using radiofrequency (RF), Bluetooth, acoustic, or infrared technology.

After use, needle electrodes 12a, 12b may be removed from the patient by first pulling the tab 54 of the needle electrode fixation device 10 away from the patient. As the needle electrodes 12a, 12b are withdrawn from the patient's skin, biasing member 24 acts to quickly bias the needle electrodes 12a, 12b back into recesses 42a, 42b so as to minimize exposure of the tips 12a', 12b' to the health care provider.

Figure 4:
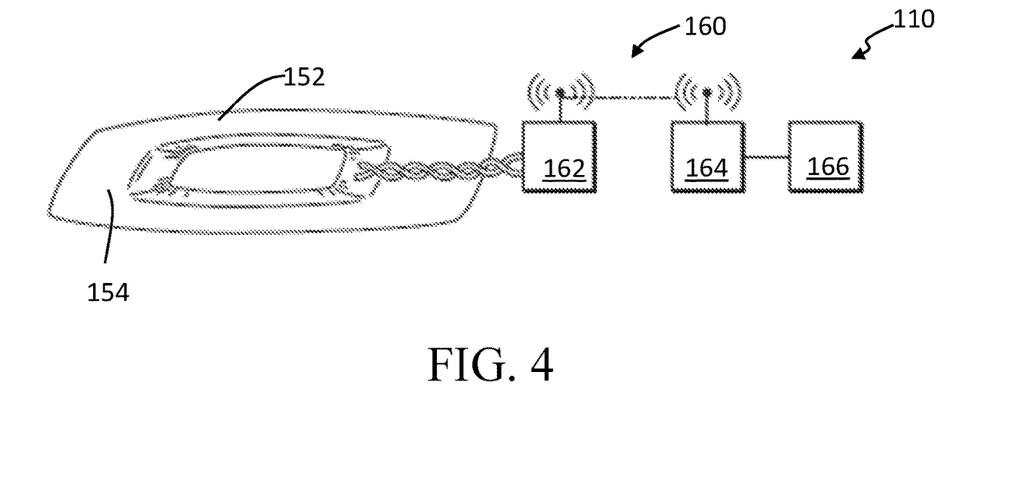
FIG. 4 depicts another needle electrode fixation device that includes a cover, an adhesive layer, a base, two needle electrodes, and a wireless control unit.
Figure 5:
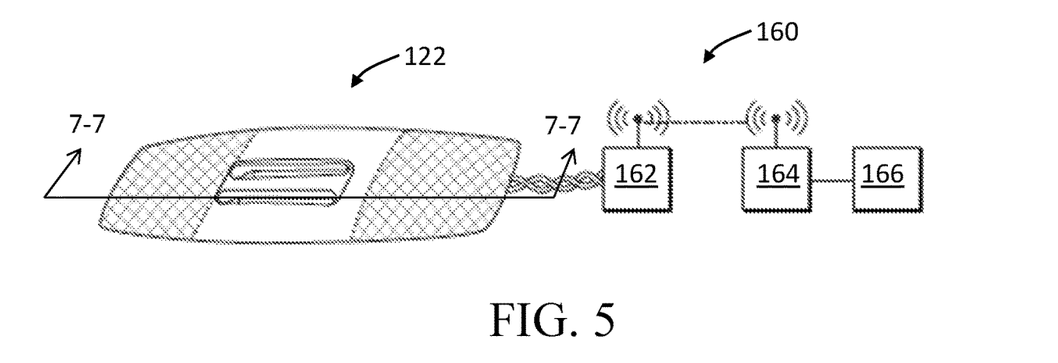
FIG. 5 depicts the base and wireless control unit of the needle fixation device shown in FIG. 4.

FIGS. 4, 5, 6, 7A, and 7B depict another needle electrode fixation device 110. Like needle electrode fixation device 10, needle electrode fixation device 110 may be connected to a control system 160 which processes and displays electrophysiological signals as they are picked by recording electrodes. As shown in FIGS. 4 and 5, control system 160 is wireless and includes a first wireless transceiver 162 mounted on the needle electrode fixation device 110 as well as a second wireless transceiver 164 connected to a processing unit 166. The first wireless transceiver 162 and the second wireless transceiver 164 are connected, for example, via radiofrequency (RF), Bluetooth, acoustic, or infrared technology. In alternative embodiments, needle electrodes 12a, 12b may be hard wired to the control system 160, including processing unit 166.

Needle electrode fixation device 110 further includes an adhesive layer 150 (shown in FIGS. 7A and 7B) and a cover 152. Adhesive layer 150 is configured to secure the device 110 to the surface of the patient's skin. Adhesive layer 150 has a top adhesive surface configured to attach to a base 120 of the needle electrode fixation device 110 and a bottom adhesive surface configured to attach to the patient's skin. Like adhesive layer 50, adhesive layer 150 and its bottom layer may be comprised of biocompatible materials including acrylates (e.g., methacrylates and epoxy diacrylates) and other materials commonly used for securing bandages, wraps, and other medical devices to human skin. Cover 152 is affixed to the top of base 120 and may include an interference artifact shield configured to minimize electrical interference that might otherwise be detected by the needle electrodes 12a, 12b. Portions of the adhesive layer 150 and the cover 152 overlap the base 120 so as to together form a tab 154 that may be used to enable removal of the needle electrode fixation device 110.

Figure 6:
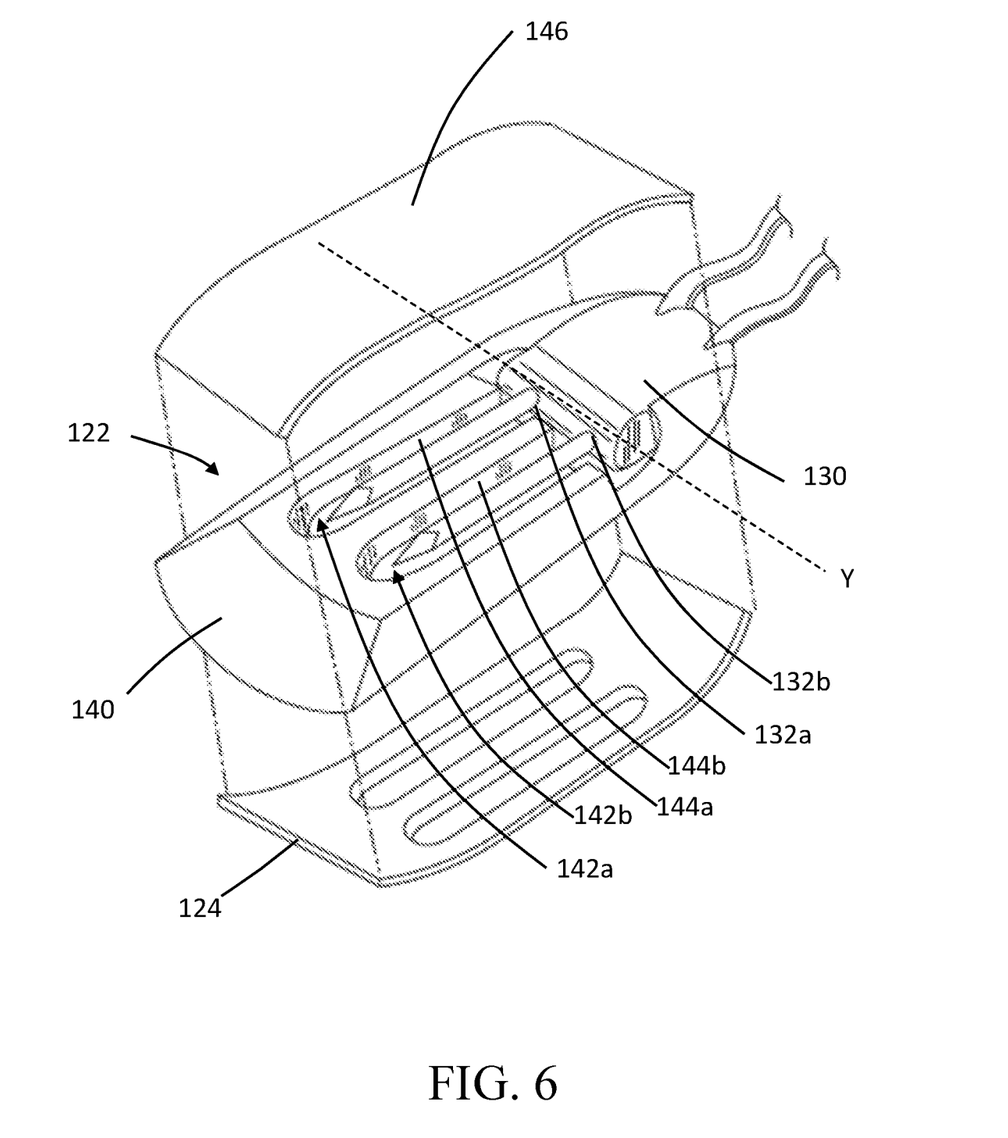
FIG. 6 is an exploded view of the base and two needle electrodes of the needle fixation device shown in FIG. 4.
Figure 7A:
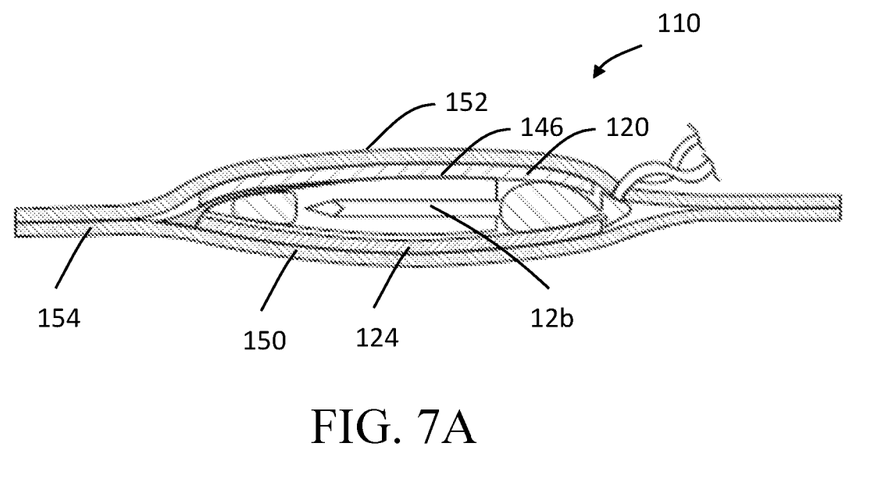
FIGS. 7A and 7B are cross-sectional views of the needle fixation device shown in FIG. 4 taken along sectional line 7-7.
Figure 7B:
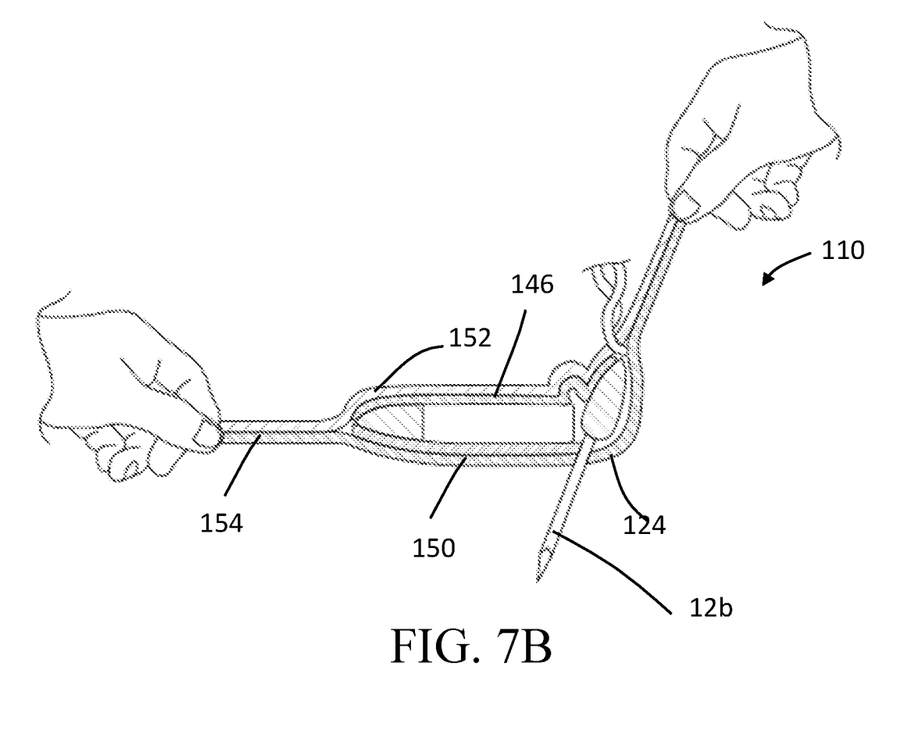

With reference to FIG. 6, base 120 includes a body 122 that defines a first portion 130 and a second portion 140. The first portion 130 is configured to move relative to the second portion 140. For example, first portion 130 may be configured to rotate relative to second portion 140 about an axis Y (shown in FIG. 3). Body 122 of base 120 is formed such the first portion 130 and the second portion 140 are rotatable in relation to one another such that the device 110 is self-capping to cover needle tips 12a', 12b' when they are not inserted into the patient's skin. In some examples, device 110 may be further configured so as to form to curvatures of portions of the surface of the patient's skin. Body 122 may be injection molded as a single piece.

First portion 130 defines channels 132a, 132b configured to fit needle electrodes 12a, 12b, respectively. Channels 132a, 132b extend through first portion 130. Channels 132a, 132b may be circular and define diameters that are slightly larger than the diameters of needle electrodes 12a, 12b such that needle electrodes 12a, 12b pass through channels 132a, 132b and lateral movement is minimized. In alternative embodiments, first portion 130 may have a single channel that is large enough to fit both needle electrodes 12a, 12b.

As shown in FIG. 6, second portion 140 defines recesses 142a, 142b that correspond to channels 132a, 132b and are configured to fit the tips 12a', 12b' of needle electrodes 12a, 12b. Recesses 142a, 142b may each be defined by side surface 144a, 144b and a protective layer 146 that is disposed between the body 122 and the cover 152. Protective layer 146 may include a plastic material, such as polycarbonate, polyethylene, polypropylene, or another material that is resistant to puncture from needle electrodes 12a, 12b. Protective layer 146 is configured to minimize the likelihood that needle electrodes 12a, 12b will protrude through the upper surface of the base 120. In alternative embodiments, a single recess may be configured to fit both tips 12a', 12b'. For example, a single recess may extend between the outer of each of sidewalls 44a and 44b and be further defined by the protective layer 146.

An elastomer layer 124 is disposed between the body 122 and the adhesive layer 150 and is configured to bias the first portion 130 into a rotatable position relative to the second portion 140 about axis Y such that needle electrodes 12a, 12b are disposed in recesses. Specifically, elastomer layer 124 imparts opposite rotational forces on the first portion 130 and the second portion 140 about axis Y so as to pull second portion 140 down around needle electrodes 12a, 12b.

Prior to use, tips 12a', 12b' of needle electrodes 12a, 12b may be inserted through channels 132a, 132b and into recesses 142a, 142b. Adhesive layer 150 and elastomer layer 124 may be affixed to base 120 before or after needle electrodes 12a, 12b are inserted into channels 132a, 132b. Adhesive layer 150 and elastomer layer 124 may each have an aperture, or multiple apertures that correspond to recesses 142a, 142b such that the tips 12a', 12b' of the needle electrodes 12a, 12b can pass from recesses 142a, 142b through the adhesive layer 150. Cover 152 and protective layer 146 may also be secured to base 120 before or after needle electrodes 12a, 12b are inserted through base 120.

In one example, base 120 is first disposed on top of the elastomer layer 124, which is disposed on top adhesive surface of adhesive layer 150. Cover 152 is then disposed on top of the protective layer 146, which is disposed on top of the base 120 and the adhesive layer 150 so as to cover any of the top adhesive surface of the adhesive layer 150 that is not covered by the base 120. Tips 12a', 12b' of needle electrodes 12a, 12b then puncture through cover 152 into channels 132a, 132b, and into recesses 142a, 142b. Before or after insertion into the base 120, needle electrodes 12a, 12b may be connected to electrode leads 14a, 14b. Alternatively, needle electrodes 12a, 12b may be inserted into base 120 prior to affixing base 120 to the top adhesive surface of the adhesive layer 150. Cover 152 may then be affixed utilizing a cutout configured such that cover 152 can wrap below the electrode leads 14a, 14b.

Similar to the method described above in relation to needle electrode fixation device 10, in order to insert electrodes 12a, 12b into the patient, base 120 is flexed about axis Y so as to overcome the force of elastomer layer 124 such that needle electrodes 12a, 12b are exposed from recesses 142a, 142b. The healthcare provider then inserts the tips 12a', 12b' of the exposed needle electrodes into the patient's skin. Once the needle electrodes 12a, 12b are inserted into the patient's skin, elastomer layer 124 again places opposite rotational forces on first portion 130 and second portion 140 to rotate first portion 130 and second portion 140 about axis Y. Specifically, second portion 140 moves relative to first portion 130 so as to conform to the contours of the patient's skin. The adhesive layer 150 is then affixed to the surface of the patient's skin such that second portion 140 is disposed above needle electrodes 12a, 12b.

Once secured to the patient, and as described above, needle electrodes 12a, 12b are configured to send and receive signals to and from control system 160. After use, needle electrodes 12a, 12b may be removed from the patient by first pulling the tab 154 of the needle electrode fixation device 110 away from the patient. As the needle electrodes 12a, 12b are withdrawn from the patient's skin, elastomer layer 124 acts to quickly bias the needle electrodes 12a, 12b back into recesses 142a, 142b so as to minimize exposure of the tips 12a', 12b' to the health care provider.

Figure 8A:
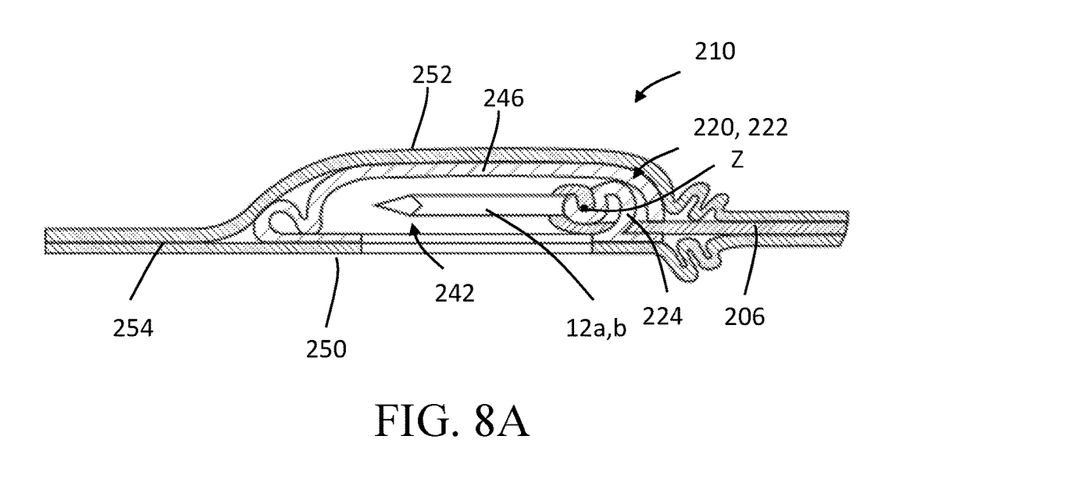
FIGS. 8A and 8B are cross-sectional views of a third needle fixation device that includes a cover, an adhesive layer, a base, and two needle electrodes.
Figure 8B:
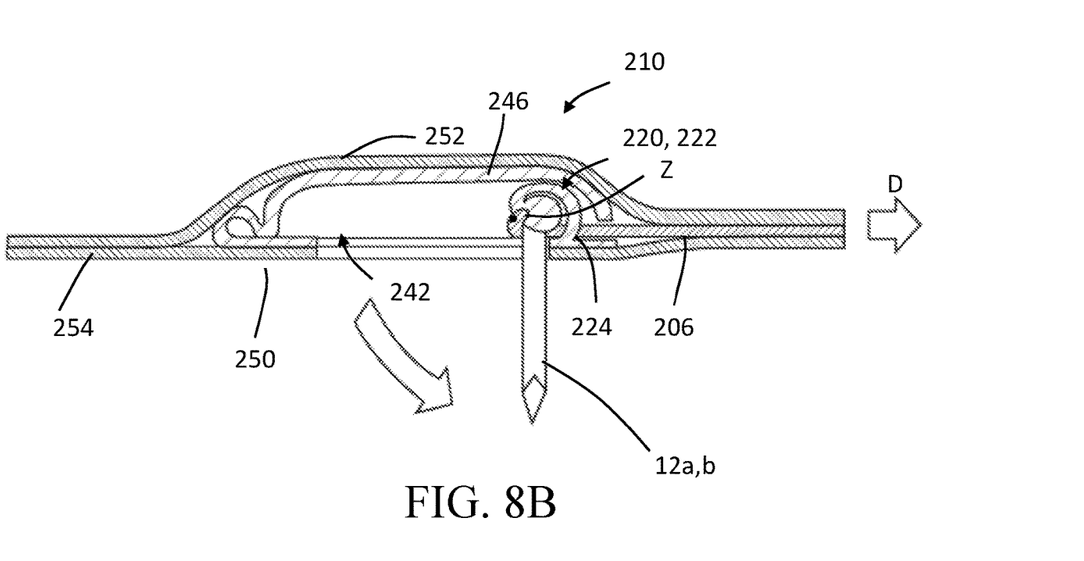

FIGS. 8A, and 8B depict a third needle electrode fixation device 210. Like needle electrode fixation devices 10 and 110, needle electrode fixation device 110 may be connected to a control system (not shown) which processes and displays electrophysiological signals as they are picked by recording electrodes.

Needle electrode fixation device 210 further includes an adhesive layer 250 and a cover 252. Adhesive layer 250 is configured to secure the device 210 to the surface of the patient's skin. Adhesive layer 250 has a top adhesive surface configured to attach to a base 220 of the needle electrode fixation device 210 and a bottom adhesive surface configured to attach to the patient's skin. Like adhesive layers 50 and 150, adhesive layer 150 and its bottom layer may be comprised of biocompatible materials including acrylates (e.g., methacrylates and epoxy diacrylates) and other materials commonly used for securing bandages, wraps, and other medical devices to human skin. Cover 252 is affixed to the top of base 220 and may include an interference artifact shield configured to minimize electrical interference that might otherwise be detected by the needle electrodes 12a, 12b. Portions of the adhesive layer 250 and the cover 252 overlap the base 220 so as to together form a tab 254 that may be used to enable removal of the needle electrode fixation device 210.

Base 220 includes a body 222 which defines at least one recess 242 in which a tether 206 and a biasing member 224 are disposed. Tether 206 and biasing member 224 are each configured to rotate needle electrodes 12a, 12b in opposite directions about an axis Z (shown as a point in FIGS. 8A and 8B and extending perpendicular to the page). For example, in FIG. 8A, biasing member 224 is imparting a rotational force on needle electrodes 12a, 12b to rotate needle electrodes 12a, 12b into the at least one recess 142. In FIG. 8B, tether 206 has been pulled in a direction D that is perpendicular to axis Z so as to overcome the rotational force of biasing member 224 and rotate needle electrodes 12a, 12b out of the at least one recess 142.

Body 222 of base 220 may be formed of a flexible material such that the device 210 is self-capping to cover needle tips 12a', 12b' when they are not inserted into the patient's skin. In some examples, device 210 may be further configured so as to form to curvatures of portions of the surface of the patient's skin. Body 222 may also include a protective layer 246 that is disposed between the body 222 and the cover 252. Like protective layer 146, protective layer 246 may include a plastic material, such as polycarbonate, polyethylene, polypropylene, or another material that is resistant to puncture from needle electrodes 12a, 12b. Protective layer 246 is configured to minimize the likelihood that needle electrodes 12a, 12b will protrude through the upper surface of the base 220. In some embodiments, a single recess may be configured to fit both tips 12a', 12b'. In other embodiments, each tip 12a', 12b' may be disposed in a separate recess.

Prior to use, tips 12a', 12b' of needle electrodes 12a, 12b may be inserted into the base 220. As described above, adhesive layer 250 may be affixed to base 220 before or after needle electrodes 12a, 12b are inserted into the base. Adhesive layer 250 may have an aperture, or multiple apertures that correspond to the at least one recesses 242 such that the tips 12a', 12b' of the needle electrodes 12a, 12b can pass from the at least one recesses 242 through the adhesive layer 250. Cover 252 may also be secured to base 220 before or after needle electrodes 12a, 12b are inserted through base 220.

In order to insert electrodes 12a, 12b into the patient, tether 206 is pulled in direction D so as to overcome the force of the biasing member 224 such that needle electrodes 12a, 12b rotate about axis Z and are exposed from the at least one recess 142. The healthcare provider then inserts the tips 12a', 12b' of the exposed needle electrodes into the patient's skin. Once the needle electrodes 12a, 12b are inserted into the patient's skin, adhesive layer 150 is then affixed to the surface of the patient's skin such that tether 206 remains taught in direction D and needle electrodes 12a, 12b remain rotated about axis Z.

Once secured to the patient, and as described above, needle electrodes 12a, 12b are configured to send and receive signals to and from the control system. After use, needle electrodes 12a, 12b may be removed from the patient by first pulling the tab 254 of the needle electrode fixation device 210 away from the patient. As the needle electrodes 12a, 12b and adhesive layer 250 are removed from the patient, tether 206 is released and biasing member 224 acts to quickly pull the needle electrodes 12a, 12b back into the at least one recess 242 so as to minimize exposure of the tips 12a', 12b' to the health care provider.

Additional changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. A needle electrode fixation device configured to secure at least one transdermal needle electrode to a patient, the device comprising:
   a base having a body that defines a first portion and a second portion, the first and second portions being rotatable relative to each other,
      the first portion defining a housing having proximal and distal ends, and a preformed interior channel running from the proximal end to the distal end, the channel configured to fit a portion of the at least one transdermal needle electrode,
      the second portion defining at least one recess configured to fit a tip of the the at least one transdermal needle electrode; and
   an adhesive layer configured to affix the base to the patient.

2. The needle electrode fixation device of claim 1, the recess being partially defined by a top portion of the body that is disposed above the at least one transdermal needle electrode and configured to prevent the at least one transdermal needle electrode from protruding through the top of the device.

3. The needle electrode fixation device of claim 1 further comprising a cover disposed on top of the base and the adhesive layer.

4. The needle electrode fixation device of claim 3, the cover further comprising an interference artifact shield.

5. The needle electrode fixation device of claim 1,
the at least one transdermal needle electrode comprising first and second transdermal needle electrodes; and
the recess being configured to fit a tip of the first and second transdermal needle electrodes.

6. The needle electrode fixation device of claim 1,
the at least one transdermal needle electrode comprising first and second transdermal needle electrodes; and
the at least one recess comprising first and second recesses, the first recess configured to fit a tip of the first transdermal needle electrode, and the second recess configured to fit a tip of the second transdermal needle electrode.

7. A needle electrode fixation device configured to secure at least one transdermal needle electrode to a patient, the device comprising:
a base having a body that defines a first portion and a second portion, the first and second portions being rotatable relative to each other;
the first portion defining a housing having proximal and distal ends, and a preformed interior channel running from the proximal end to the distal end, the channel configured to fit a portion of the at least one transdermal needle electrode such that at least one axis of the channel defines a diameter only slightly larger than a diameter of the at least one transdermal needle electrode; and
the second portion defining at least one recess configured to fit a tip of the the at least one transdermal needle electrode;
wherein the needle electrode fixation device is configured to minimize movement of the at least one transdermal needle electrode relative to the first portion.

8. The needle electrode fixation device of claim 1, the first portion and the second portion each further comprising a bottom surface possessing an adhesive layer, said adhesive layer further comprising an elastic portion that biases the bottom surface of the first portion at an angle relative to the bottom surface of the second portion.

9. The needle electrode fixation device of claim 1 further comprising a wireless transmitter that is configured to send signals from the at least one transdermal needle electrode to a control system.

10. The needle electrode fixation device of claim 7 further comprising an adhesive layer configured to affix the base to the patient.

11. The needle electrode fixation device of claim 7, the recess being partially defined by a top portion of the body that is disposed above the at least one transdermal needle electrode and configured to prevent the at least one transdermal needle electrode from protruding through the top of the device.

12. The needle electrode fixation device of claim 7 further comprising a cover disposed on top of the base and an adhesive layer.

13. The needle electrode fixation device of claim 12, the cover further comprising an interference artifact shield.

14. The needle electrode fixation device of claim 7,
the at least one transdermal needle electrode comprising first and second transdermal needle electrodes; and
the recess being configured to fit a tip of the first and second transdermal needle electrodes.

15. The needle electrode fixation device of claim 7,
the at least one transdermal needle electrode comprising first and second transdermal needle electrodes; and
the at least one recess comprising first and second recesses, the first recess configured to fit a tip of the first transdermal needle electrode, and the second recess configured to fit a tip of the second transdermal needle electrode.

16. The needle electrode fixation device of claim 7 further comprising a wireless transmitter that is configured to send signals from the needle electrode to a control system.

17. The needle electrode fixation device of claim 7, further comprising a biasing member that connects the first portion and the second portion.

18. A needle electrode fixation device configured to secure at least one transdermal needle electrode to a patient, the device comprising:
a base having a body that defines a first portion and a second portion, the first and second portions being rotatable relative to each other,
the first portion defining a housing having proximal and distal ends, the housing having a preformed interior channel running from the proximal end to the distal end, the channel configured in relationship to the at least one transdermal needle electrode to receive the at least one transdermal needle electrode from the proximal end and minimize lateral movement of the at least one transdermal needle electrode in the channel; and
the second portion defining at least one recess configured to fit a tip of the at least one transdermal needle electrode.

* * * * *